(12) United States Patent
Lorant

(10) Patent No.: US 9,717,658 B2
(45) Date of Patent: Aug. 1, 2017

(54) O/W EMULSIONS CONTAINING A HYDROPHOBIC MODIFIED INULIN AND AT LEAST ONE THICKENING POLYSACCHARIDE OF PLANT ORIGIN

(75) Inventor: Raluca Lorant, Thiais (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/809,833

(22) PCT Filed: Dec. 17, 2008

(86) PCT No.: PCT/EP2008/067770
§ 371 (c)(1),
(2), (4) Date: Sep. 16, 2010

(87) PCT Pub. No.: WO2009/080659
PCT Pub. Date: Jul. 2, 2009

(65) Prior Publication Data
US 2010/0331429 A1    Dec. 30, 2010

Related U.S. Application Data

(60) Provisional application No. 61/021,048, filed on Jan. 15, 2008.

(30) Foreign Application Priority Data

Dec. 20, 2007 (FR) ..................................... 07 60164
Feb. 18, 2008 (FR) ..................................... 08 51017

(51) Int. Cl.
| | |
|---|---|
| *A61K 8/73* | (2006.01) |
| *A61Q 19/00* | (2006.01) |
| *A61Q 1/14* | (2006.01) |
| *A61K 8/06* | (2006.01) |
| *B01F 17/00* | (2006.01) |

(52) U.S. Cl.
CPC ............... *A61K 8/062* (2013.01); *A61K 8/73* (2013.01); *A61K 8/731* (2013.01); *A61K 8/732* (2013.01); *A61K 8/733* (2013.01); *A61K 8/737* (2013.01); *A61Q 19/00* (2013.01); *B01F 17/0028* (2013.01); *A61K 2800/48* (2013.01); *A61K 2800/594* (2013.01); *A61Q 1/14* (2013.01)

(58) Field of Classification Search
CPC .......... A61K 2800/48; A61K 2800/594; A61K 8/062; A61K 8/73; A61K 8/731; A61K 8/732; A61K 8/733; A61K 8/737; A61Q 19/00; A61Q 1/14; B01F 17/0028; G06F 17/5027; H03K 19/017581; H03K 19/17748

See application file for complete search history.

(56) References Cited

U.S. PATENT DOCUMENTS 6,534,647 B1 *  3/2003  Stevens ................... C07H 3/00
                                                    536/115

FOREIGN PATENT DOCUMENTS

| EP | 1 586 307 | 10/2005 | |
|---|---|---|---|
| EP | 1 920 752 | 5/2008 | |
| WO | 2004 030544 | 4/2004 | |
| WO | WO 2006121880 | * 11/2006 | ............... A61Q 1/10 |
| WO | 2007 017196 | 2/2007 | |
| WO | 2007 090554 | 8/2007 | |

OTHER PUBLICATIONS

Hall (Biotemplating: complex structures from natural materials; Imperial College Press 2009 pp. 28-30) 3 pages.*
Taylor (Marine Medicinal Foods; Academic Press 2011; p. 259). 2 pages.*
DERWENT-ACC-No. 2007-283410 abstracting WO 2007017196 published Jun. 7, 2007; 7 pages.*
English translation of WO2007017196 A2 (Hloucha).*
English translated claims to WO 2007017196; 2007; 1 page.*
English translated EP1424991 Jun. 9, 2004; 2 pages.*
DERWENT-ACC-No. 2004-092844 Allwohn J Abstract of EP 1371353; published Dec. 17, 2003; 6 pages.*
Kays et al. Biology and Chemistry of Jerusalem Artichoke 2007, CRC Press p. 68-69 and 78; 3 pages.*
English translation of WO 2008003685 Jan. 1, 2008; 13 pages.*
Stevens et al. Polymeric surfactants based on Inulin, Biomacromolecules, 2001;2:1256-1259.*
Booten, K., et al., "Polymeric, Carbohydrate-Based Surfactants and Their Use in Personal Care Applications", SOFW, Journal Seifen, Oele, Fette, Wachse, Verlag Fur Chemische Industrie, Augsburg, XP002416632, vol. 130, No. 8, pp. 10-16 (Jan. 1, 2004).
Woodruff, J. "Personal Care Feature: Bathroom Products 2005" XP002491404, Retrieved from the Internet: URL:http://www.creative-developments.co.uk/papers/Bathroom%20Feature%202005. pdf, Published in SPC: Feb. 2005.
U.S. Appl. No. 12/809,835, filed Jun. 21, 2010, Lorant.
U.S. Appl. No. 12/809,869, filed Jun. 21, 2010, Lorant.
U.S. Appl. No. 14/261,735, filed Apr. 25, 2014, Lorant.
English translation of the Japanese Office Action issued Aug. 6, 2013 in Patent Application No. 2010-538710.

(Continued)

*Primary Examiner* — Ernst V Arnold
(74) *Attorney, Agent, or Firm* — Oblon, McClelland, Maier & Neustadt, L.L.P.

(57) ABSTRACT

The invention relates especially to a composition in the form of an oil-in-water emulsion comprising an inner fatty phase and an outer aqueous phase and containing: a) at least 0.01% by weight and preferably at least 0.05% by weight, relative to the total weight of the composition, of at least one inulin modified with hydrophobic chains, and b) at least 0.05% by weight and preferably at least 0.1% by weight, relative to the total weight of the composition, of at least one thickening polysaccharide of plant origin, the said composition being free of silicones. The invention also relates to a cosmetic process using the said composition.

9 Claims, No Drawings

(56) References Cited

OTHER PUBLICATIONS

Shigeru Sekine, New Cosmetic Handbook, Nikko Chemicals Co. Ltd. Oct. 30, 2006, 30 Pages (submitting English translation only).

* cited by examiner

O/W EMULSIONS CONTAINING A HYDROPHOBIC MODIFIED INULIN AND AT LEAST ONE THICKENING POLYSACCHARIDE OF PLANT ORIGIN

CROSS-REFERENCE TO RELATED APPLICATIONS

This application is the National stage of PCT/EP08/067770, filed Dec. 17, 2013, the disclosure of which is incorporated herein by reference, in its entirety. The parent application claims priority to U.S. Provision Application 61/021,048, filed Jan. 15, 2008, the disclosure of which is incorporated herein by reference, in its entirety. The parent application also claims priority to French Application No. 0760164, filed Dec. 20, 2007, and French Application No. 0851017, filed Feb. 18, 2008, the disclosures of which are incorporated herein by reference, in their entireties

BACKGROUND OF THE INVENTION

The field of the invention concerns compositions in the form of stable oil-in-water (O/W) emulsions especially having very good cutaneous tolerance.

Preferably, the compositions according to the invention are natural.

According to the invention, the term "natural compositions" means compositions predominantly or even exclusively comprising ingredients of natural origin, as opposed to ingredients of petrochemical or synthetic origin.

The invention relates especially to a composition in the form of an oil-in-water (O/W) emulsion containing, in a physiologically acceptable medium, at least one inulin modified with hydrophobic chains and at least one polysaccharide of plant origin.

Inulin modified with hydrophobic chains is used in the composition of the invention especially as an emulsifier.

The polysaccharide of plant origin is used in the composition of the invention especially as an emulsion thickener and stabilizer.

In recent years, the cosmetic market has been marked by a very strong demand for formulations containing ingredients of natural origin. Consumers desire formulations free of chemical substances, to which they prefer ingredients of natural origin, renowned for their better tolerance and affinity with the skin.

Specifically, it is known that emulsifying surfactants and synthetic polymers (e.g.: acrylic polymers), emulsion stabilizers and texturizers, although being very effective, are liable to have an irritant potential, in particular in the case of people with sensitive or reactive skin.

There is thus still a need for compositions in the form of an oil-in-water (O/W) emulsion that are stable, even in the absence of emulsifiers and/or stabilizers/texturizers of synthetic origin.

DETAILED DESCRIPTION OF THE INVENTION

The Applicant has shown, surprisingly, that a combination of an inulin modified with hydrophobic chains, in particular an inulin lauryl carbamate combined with at least one polysaccharide of plant origin, can satisfy this need.

The inulin lauryl carbamate proposed by the company Orafti under the name Inutec SP1®, despite its amphiphilic nature, has poor emulsifying properties and does not allow stable emulsions to be obtained when it is used as sole emulsifier. The stabilization of such compositions may be obtained with standard emulsifying and/or thickening systems, comprising surfactants (e.g. sugar esters, alkyl polyglucosides or polyglycerolated esters); polysaccharides of biotechnological or synthetic origin (e.g. xanthan gum in combination with Veegum (magnesium aluminium silicate); fatty alcohols and/or hydrophobic acrylic polymers (e.g. acrylate/$C_{10-30}$ alkyl acrylate crosspolymer=Pemulen).

However, these complex systems containing thickeners and surfactants in large amounts have the drawback of sensorily making the textures heavy and of giving a tacky, sticky feel and a certain irritant potential.

The combination that is the subject of the invention makes it possible, on the other hand, to obtain a composition in oil-in-water form that shows good stability over time, without having the texture and irritant-potential drawbacks associated with the presence of emulsifiers and/or thickeners of synthetic origin of the compositions of the prior art.

The term "good stability" means herein a homogeneous and uniform oil-in-water emulsion that does not dephase (separation of the aqueous phase and the oily phase) or exude oil, at least for two months at 37° C., or even two months at 45° C.

The use of this combination thus makes it possible to reduce the content of emulsifiers and/or thickeners of synthetic origin present in the formulation, or even to dispense with them altogether, for an "entirely natural" composition.

The composition according to the invention has the advantage of being very stable over time and of being sensorily pleasant, even in the absence of silicones or of fatty substances of petrochemical nature.

The invention especially relates to a composition in the form of an oil-in-water emulsion comprising an inner fatty phase and an outer aqueous phase and containing a) at least 0.01% by weight and preferably at least 0.05% by weight, relative to the total weight of the composition, of at least one inulin modified with hydrophobic chains, and b) at least 0.05% by weight and preferably at least 0.1% by weight, relative to the total weight of the composition, of at least one thickening polysaccharide of plant origin, the said composition being free of silicones.

According to the invention, the expression 'free' of silicones means compositions containing less than 1%, preferably less than 0.5%, or even less than 0.2% by weight, or 0% by weight, of silicones.

According to one particular mode, the invention relates to a composition in the form of an oil-in-water emulsion comprising an inner fatty phase and an outer aqueous phase comprising at least 0.05% by weight, relative to the total weight of the composition, of at least one inulin modified with hydrophobic chains, and at least 0.05% by weight, relative to the total weight of the composition, of at least one thickening polysaccharide of plant origin, the said composition being free of silicones.

According to one particular mode, the fatty phase represents at least 2% by weight and preferably at least 5% by weight relative to the total weight of the said composition.

The fatty phase may contain any type of fatty substance used in cosmetics.

According to one particular mode, the composition according to the invention in the form of an oil-in-water (O/W) emulsion comprises, in a physiologically acceptable medium:

A) an aqueous phase containing at least 0.05% by weight, relative to the total weight of the composition, of an inulin modified with hydrophobic chains, and at least 0.2% by weight, relative to the total weight of the composition, of at least one gelling and/or thickening polysaccharide of plant origin;

B) a fatty phase, which may contain any type of fatty substance used in cosmetics, the said composition being free of silicones.

The compositions according to the invention are in the form of O/W emulsions, and are preferably free of surfactants and/or of synthetic emulsifying polymers.

According to the invention, the expression "free" of surfactant and/or of synthetic emulsifying polymer means compositions containing less than 1%, preferably less than 0.5%, or even less than 0.2% by weight, or 0% by weight, of surfactant and/or of synthetic emulsifying polymer.

According to one particular embodiment, the composition according to the invention is free of fatty substances of petrochemical origin.

The term "free of fatty substances of petrochemical or synthetic origin" means that the composition comprises less than 1% by weight of fatty substances of petrochemical origin, relative to the total weight of the composition, especially less than 0.5% by weight and preferably less than 0.1%, and even more preferentially contains no fatty substance of petrochemical origin.

Hydrophobic Modified Inulin

According to the invention, the term "hydrophobic modified inulin" especially means an inulin modified with hydrophobic chains, in particular modified by grafting hydrophobic chains onto the hydrophilic backbone of the said inulin.

Inulin belongs to the fructan family.

Fructans or fructosans are oligosaccharides or polysaccharides comprising a sequence of anhydrofructose units optionally combined with one or more saccharide residues other than fructose. Fructans may be linear or branched. The fructans may be products obtained directly from a plant or microbial source, or alternatively products whose chain length has been modified (increased or reduced) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are mostly linked together via β-2-1 bonds. These are essentially linear fructans such as inulins.

The second group also corresponds to linear fructoses, but the fructose units are essentially linked together via β-2-6 bonds. These products are levans.

The third group corresponds to mixed fructans, i.e. fructans containing β-2-6 and β-2-1 sequences. These are essentially branched fructans such as graminans.

Inulin may be obtained, for example, from chicory, dahlia or Jerusalem artichoke. Preferably, the inulin used in the composition according to the invention is obtained, for example, from chicory.

The inulins used in the compositions according to the invention are hydrophobic-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; cycloaliphatic divalent groups or organopolysiloxane chains. These hydrocarbon-based or organopolysiloxane chains may especially comprise one or more ester, amide, urethane, carbamate, thiocarbamate, urea, thiourea and/or sulfonamide functions such as, especially, methylenedicyclohexyl and isophorone; or aromatic divalent groups such as phenylene.

In particular, the inulin has a degree of polymerization from 2 to about 1000 and preferably from to about 60, and a degree of substitution of less than 2 on the basis of one fructose unit.

According to one preferred embodiment, the hydrophobic chains contain at least one alkyl carbamate group of formula R—NH—CO— in which R is an alkyl group containing from 1 to 22 carbon atoms.

According to one more preferred embodiment, the hydrophobic chains are lauryl carbamate groups.

In particular, as non-limiting illustrations of hydrophobic modified inulins that may be used in the compositions according to the invention, mention may be made of stearoyl inulin, such as the products sold under the names Lifidrem INST by the company Engelhard and Rheopearl INS by the company Ciba; palmitoyl inulin; undecylenoyl inulin, such as the products sold under the names Lifidrem INUK and Lifidrem INUM by the company Engelhard; and inulin lauryl carbamate, such as the product sold under the name Inutec SP1 by the company Orafti.

In particular, an inulin grafted with lauryl carbamate is used, which is obtained especially from the reaction of lauryl isocyanate with an inulin, in particular obtained from chicory. An example of these compounds that may especially be mentioned is the product sold under the name Inutec SP1 by the company Orafti.

The content of hydrophobic modified inulin in the composition of the invention may range from 0.01% to 20% by weight, preferably from 0.01% to 10% by weight, in particular from 0.05% to 10% by weight, preferably from 0.1% to 10% by weight, better still from 0.1% to 5% by weight and even more preferentially from 0.1% to 1% by weight of active material relative to the total weight of the said composition.

The content of hydrophobic modified inulin is chosen as a function of the content of fatty substance present in the said composition.

Preferably, the weight ratio of hydrophobic modified inulin/fatty substance may range from 1:0.1 to 0.1:60, in particular from 0.1:1 to 0.1:60, preferably from 0.1:1 to 0.1:15, more preferentially from 0.1:5 to 0.1:15 and even more preferentially from 0.1:8 to 0.1:12.

Preferably, it will be 0.1:10, i.e. 0.1% inulin per 10% fatty substance by weight relative to the total weight of the composition.

By way of example:

| Weight percentage of hydrophobic modified inulin relative to the total weight of the composition | Weight percentage of fatty substance relative to the total weight of the composition | Weight ratio (hydrophobic modified inulin/fatty substance) |
| --- | --- | --- |
| 0.1 | 60 | 0.0017 |
| 0.1 | 40 | 0.0025 |
| 0.1 | 20 | 0.005 |
| 0.1 | 15 | 0.0067 |
| 0.1 | 12 | 0.0083 |
| 0.1 | 10 | 0.01 |
| 0.1 | 8 | 0.0125 |
| 0.1 | 5 | 0.02 |
| 1 | 0.1 | 10 |

It may also be stated that the weight ratio (modified inulin/fatty substance) ranges from 0.001 to 10, in particular from 0.002 to 10, preferably from 0.005 to 10 and better still from 0.005 to 0.02.

Preferably, the weight ratio (hydrophobic modified inulin/fatty substance) will be less than 1, especially less than 0.5 and better still less than 0.1.

In particular, it will be 0.01.

The hydrophobic modified inulin may be, alternatively, dispersed in the aqueous phase or the oily phase, before emulsification.

Preferably, it will be dispersed in the oily phase before emulsification.

Thickening Polysaccharides of Natural Origin

These polysaccharides act as thickener and stabilizer for the composition according to the invention.

Polysaccharide of Plant Origin

The composition according to the invention contains at least one polysaccharide of plant origin.

According to the invention, the term "polysaccharide of plant origin" especially means a polysaccharide obtained from the plant kingdom (plants or algae), as opposed to a polysaccharide obtained via biotechnology, as is the case, for example, for xanthan gum, which is produced especially by fermentation of a bacterium, *Xanthomonas campestris*.

This plant-derived polysaccharide may, where appropriate, be chemically modified to promote its hydrophilic valency, as is the case for cellulose derivatives, in particular hydroxyalkyl celluloses (e.g.: hydroxyethylcellulose).

As examples of polysaccharides of plant origin that may be used according to the invention, mention may be made especially of:
a) algal extracts, such as alginates, carrageenans and agars, and mixtures thereof. Examples of carrageenans that may be mentioned include Satiagum UTC30® and UTC10® from the company Degussa; an alginate that may be mentioned is the sodium alginate sold under the name Kelcosol® by the company ISP;
b) gums, such as guar gum and nonionic derivatives thereof (hydroxypropyl guar), gum arabic, konjac gum or mannan gum, gum tragacanth, ghatti gum, karaya gum or locust bean gum; examples that may be mentioned include the guar gum sold under the name Jaguar HP105® by the company Rhodia; the mannan and Konjac Gum® (1% gluconomannan) sold by the company GfN;
c) modified or unmodified starches, such as those obtained, for example, from cereals, for instance wheat, corn or rice, from legumes, for instance blonde pea, from tubers, for instance potato or cassava, and tapioca starches; dextrins, such as corn dextrins; examples that may especially be mentioned include the rice starch Remy DR I® sold by the company Remy; the corn starch B® from the company Roquette; the potato starch modified with 2-chloroethylaminodipropionic acid neutralized with sodium hydroxide, sold under the name Structure Solanace® by the company National Starch; the native tapioca starch powder sold under the name Tapioca Pure® by the company National Starch;
d) dextrins, such as the dextrin extracted from corn under the name Index® from the company National Starch;
e) celluloses and derivatives thereof, in particular alkyl celluloses, hydroxyalkyl celluloses; and alkyl hydroxyalkyl celluloses; mention may be made especially of methyl-celluloses, hydroxyethylcelluloses, ethyl-hydroxyethylcelluloses and carboxymethyl-celluloses. Examples that may be mentioned include stearyl and cetyl hydroxyethylcellulose. Examples of cetyl hydroxyethylcelluloses that may be mentioned include Polysurf 67CS® and Natrosol Plus 330® from Aqualon;
and mixtures thereof.

Preferably, the thickening polysaccharide of plant origin will be chosen from an algal extract, a gum and a cellulose derivative, and mixtures thereof.

Preferably, agars, locust bean gum, mannan konjac gum, cetyl or stearyl hydroxyethylcelluloses and tapioca starches will be used.

According to a first embodiment, the thickening polysaccharide of plant origin is an algal extract chosen from alginates, carrageenans and agars, and mixtures thereof. Preferably, alginates or agars, or mixtures thereof, will be used.

According to another embodiment, the thickening polysaccharide of plant origin is chosen from a gum, such as guar gum, gum arabic, mannan and konjac gum and locust bean gum, and mixtures thereof.

According to another embodiment, the thickening polysaccharide of plant origin is a modified or unmodified starch chosen from wheat starch, corn starch, rice starch, potato starch and tapioca starch, and mixtures thereof.

According to another embodiment, the thickening polysaccharide of plant origin is a dextrin, such as corn dextrin.

According to another embodiment, the thickening polysaccharide of plant origin is a cellulose or a cellulose derivative.

The cellulose derivative may in particular be a ($C_1$-$C_3$) hydroxyalkyl cellulose, especially modified with hydrophobic chains, in particular hydrophobic group(s) containing from 8 to 30 carbon atoms.

According to one embodiment, the hydrophobic substituent(s) used is (are) $C_8$-$C_{30}$ and preferably $C_{10}$-$C_{22}$ alkyl, arylalkyl or alkylaryl groups.

Preferably, the hydrophobic substituent(s) according to the present invention is (are) saturated $C_{10}$-$C_{22}$ and preferably $C_{16}$-$C_{20}$ alkyl chains, such as cetyl ($C_{16}$), stearyl ($C_{18}$) and behenyl ($C_{20}$) groups.

According to one preferred embodiment, the hydrophobic substituent(s) according to the present invention is (are) cetyl groups.

These cellulose derivatives containing hydrophobic substituent(s) according to the invention have a viscosity preferably of between 100 and 100 000 mPa·s and preferably between 200 and 20 000 mPa·s, measured at 25° C. in a solution containing 1% by weight of polymer in water, this viscosity being determined conventionally using a viscometer of Brookfield LVT type at 6 rpm with a No. 3 spindle.

Among the cellulose derivatives containing hydrophobic substituent(s) that may be used in the compositions of the invention, mention may preferably be made of the cetyl hydroxyethylcelluloses sold under the names Natrosol Plus Grade 330 CS and Polysurf 67 CS (INCI name: cetyl hydroxyethylcellulose) by the company Aqualon/Hercules.

According to one particular embodiment of the invention, the composition comprises at least one locust bean gum. In particular, the Genu gum type RL200® from CP Kelco is used.

According to one alternative, the composition comprises at least one konjac mannan gum. In particular, Glucovis 50® from Chesham Chemicals is used.

According to another preferred mode, the composition comprises at least one cetyl hydroxyethylcellulose, in particular Polysurf 67CS® or Natrosol Plus 330 from the company Aqualon.

According to one particular mode of the invention, the composition comprises at least two thickening polysaccharides of plant origin.

The thickening polysaccharide(s) of plant origin represent(s) from 0.05% to 10%, especially from 0.1% to 10%, preferably from 0.2% to 10%, preferably from 0.2% to 5% and even more preferentially from 0.2% to 3% by weight relative to the total weight of the said composition.

Additional Polysaccharides

According to one preferred mode, the composition of the invention may also comprise at least one additional polysaccharide obtained via biotechnology.

Mention may be made especially of a linear polyglucose obtained by fermentation of *Sclerotium rofsii* as sold by Alban Müller under the name Amigum®; a polysaccharide obtained by fermentation of Rhizobium, such as Soligel® from the company Soliance; or xanthan gum, such as Rhodicare XC® from Rhodia, and xanthan gums modified with glucose/mannose/glucuronic acid groups, such as Keltrol T® from CP Kelco, Rhodicare CFT® from Rhodia, or Nomcort Z® from Nisshin Oil.

In particular, at least one xanthan gum will be used with the polysaccharide of plant origin.

Preferred combinations that may be mentioned include:
locust bean gum with an agar and/or a xanthan gum;
mannan konjac gum and xanthan gum;
a hydroxyalkyl cellulose and a xanthan gum.

According to one particular mode, the composition of the invention contains at least two gelling/thickening polysaccharides of natural origin, at least one being of plant origin.

The amount of polysaccharide(s) present in the composition of the invention depends on their thickening properties.

In general, from 0.05% to 10% by weight, preferably from 0.1% to 5% by weight and more preferentially from 0.2% to 3% by weight of polysaccharide(s) may be used relative to the total weight of the composition.

Aqueous Phase

The aqueous phase generally contains water and hydrophilic adjuvants, including monoalcohols containing 2 to 8 carbon atoms, for instance ethanol and isopropanol, and polyols, for instance glycerol, glycols, for instance pentylene glycol, propylene glycol, butylene glycol, isoprene glycol and polyethylene glycols such as PEG-8; sorbitol; sugars such as glucose, fructose, maltose, lactose or sucrose; and mixtures thereof.

The water may be a floral water such as cornflower water and/or a mineral water such as eau de Vittel, eau de Lucas or eau de La Roche Posay and/or a spring water.

The polyol that is miscible with water at room temperature (25° C.) may be chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol;

glycol ethers (especially containing from 3 to 16 carbon atoms) such as mono-, di- or tripropylene glycol ($C_1$-$C_4$) alkyl ethers or mono-, di- or triethylene glycol ($C_1$-$C_4$)alkyl ethers; and mixtures thereof.

The polyol that is miscible with water at room temperature may be present in the composition in a content ranging from 1% to 20% by weight and preferably ranging from 3% to 15% by weight relative to the total weight of the composition.

The composition according to the invention may comprise a monoalcohol containing from 2 to 6 carbon atoms, such as ethanol or isopropanol, especially in a content ranging from 0.01% to 10% by weight and preferably ranging from 1% to 7% by weight relative to the total weight of the composition.

The aqueous phase (including the polyols and other water-soluble or water-dispersible compounds) may represent from 50% to 99% by weight, in particular from 50% to 88% by weight, preferably from 60% to 85% by weight and better still from 65% to 85% by weight relative to the total weight of the composition.

Fatty Phase

The composition according to the invention preferably comprises at least 1% by weight of an inner fatty phase relative to the total weight of the composition, especially at least 2% by weight or even at least 5% by weight of an inner fatty phase relative to the total weight of the composition.

This fatty phase generally comprises an oily phase.

The inner fatty phase is present in the composition according to the invention preferably in a content ranging from 3% to 50% by weight relative to the total weight of the composition, especially from 5% to 50% by weight, preferably from 5% to 40% by weight, more preferentially from 10% to 40% by weight and more preferentially from 10% to 30% by weight, or even from 15% to 30% by weight relative to the total weight of the composition.

The oily phase is constituted of oils and of any other fatty substance or lipophilic constituent (e.g.: cosmetic active agents or UV-screening agents) that may be present in the composition of the invention.

Mention may be made especially of oils, fatty esters, waxes and butters, which may be, respectively, of natural (animal or plant) origin or synthetic origin.

Fatty substances of natural origin will preferentially be used, such as plant oils, fatty esters of plant origin and waxes or butters of plant origin.

According to one preferred embodiment of the invention, the oily phase contains at least one hydrocarbon-based oil of natural origin and/or at least one wax of natural origin.

The oily phase is a fatty phase containing at least one fatty substance chosen from volatile or non-volatile oils that are liquid at room temperature (20-25° C.), gums and pasty fatty substances, of animal, plant, mineral or synthetic origin, and mixtures thereof. These fatty substances are physiologically acceptable.

The oily phase may also comprise any common liposoluble or lipodispersible additive.

Preferably, the oily phase contains at least one oil, more particularly at least one cosmetic oil. The term "oil" means a fatty substance that is liquid at room temperature (25° C.)

The term "volatile oil" means any non-aqueous medium that is capable of evaporating from the skin or the lips in less than one hour, especially having a vapour pressure, at room temperature and atmospheric pressure, ranging from $10^{-3}$ to 300 mmHg (0.13 Pa to 40 000 Pa).

As volatile oils that may be used in the invention, it is possible to use non-silicone volatile oils, especially $C_8$-$C_{16}$ isoparaffins, for instance isododecane, isodecane or isohexadecane and, for example, the oils sold under the trade names Isopar and Permethyl, and especially isododecane (Permethyl 99 A).

The oil may also be a non-volatile oil.

The term "non-volatile oil" means an oil that is capable of remaining on the skin at room temperature (25° C.) and atmospheric pressure for at least one hour and that especially has a non-zero vapour pressure at room temperature (25° C.) and atmospheric pressure, of less than 0.01 mmHg (1.33 Pa).

As non-volatile oils that may be used in the invention, mention may be made of non-silicone and especially hydrocarbon-based non-volatile oils, such as liquid paraffin (or petroleum jelly), squalane, hydrogenated polyisobutylene (parleam oil), perhydrosqualene, mink oil, turtle oil, soybean oil, sweet almond oil, beauty-leaf oil, palm oil, grapeseed oil, sesame seed oil, corn oil, arara oil, rapeseed oil, sunflower oil, cottonseed oil, apricot oil, castor oil, avocado oil, jojoba oil, olive oil, argan oil, virgin sweet almond oil, apricot kernel oil, rice bran oil, camellia oil or cereal germ oil; as preferred oils, jojoba oil or apricot kernel oil, and mixtures thereof, will be used; lanolic acid, oleic acid, lauric acid or stearic acid esters; esters derived from long-chain acids or alcohols (i.e. chains containing from 6 to 20 carbon atoms), especially the esters of formula RCOOR' in which R represents a higher fatty acid residue containing from 7 to 19 carbon atoms and R' represents a hydrocarbon-based chain containing from 3 to 20 carbon atoms, in particular $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl)succinate, diisostearyl malate, or glyceryl or diglyceryl triisostearate; higher fatty acids, especially of $C_{14}$-$C_{22}$, such as myristic acid, palmitic acid, stearic acid, behenic acid, oleic acid, linoleic acid, linolenic acid or isostearic acid; higher fatty alcohols, especially of $C_{16}$-$C_{22}$, such as cetanol, oleyl alcohol, linoleyl alcohol, linolenyl alcohol, isostearyl alcohol or octyldodecanol; and mixtures thereof.

The choice of the oils is especially made as a function of the desired aim. Thus, the triglycerides and the plant oils such as apricot oil or olive oil are preferred for compositions intended for dry skin, whereas fatty acid esters, which are lighter, are preferred for compositions intended for normal or combination skin.

The other fatty substances that may be present in the oily phase are, for example, fatty acids containing from 8 to 30 carbon atoms, for instance stearic acid, lauric acid or palmitic acid; pasty fatty substances, for instance petroleum jelly or lanolin; waxes, for instance beeswax, carnauba wax, candelilla wax, paraffin wax, lignite wax, microcrystalline waxes, ceresin, ozokerite, synthetic waxes such as polyethylene waxes, polymethylene waxes and Fischer-Tropsch waxes.

These fatty substances may be chosen in a varied manner by a person skilled in the art in order to prepare a composition having the desired properties, for example in terms of consistency or texture.

The amount of fatty or oily phase in the composition of the invention is preferably greater than or equal to 1% by weight, preferably greater than or equal to 2% by weight, or even greater than or equal to 5% by weight, even more preferentially greater than or equal to 10% by weight, or even 20% by weight, and better still greater than or equal to 30% by weight, relative to the total weight of the composition.

It may range, for example, from 3% to 50% by weight relative to the total weight of the composition, especially from 5% to 50% by weight, preferably from 5% to 40% by weight, more preferentially from 10% to 40% by weight and more preferentially from 10% to 30%, or even from 15% to 30% by weight, relative to the total weight of the composition.

It may moreover range from 11% to 50% by weight, preferably from 12% to 40% by weight, better still from 15% to 40% by weight and even better still from 15% to 35% by weight relative to the total weight of the composition.

The compositions according to the invention may be cosmetic or dermatological compositions. They will preferably be cosmetic compositions.

The composition according to the invention contains a physiologically acceptable medium.

In the present invention, the term "physiologically acceptable medium" means a non-toxic medium that is compatible with human skin (including the interior of the eyelids), mucous membranes, hair or lips. A cosmetic composition is a product that has a pleasant appearance, odour and feel, and that is intended for topical application.

According to one preferred mode, the composition of the invention is free of surfactant.

According to the invention, the term "free" of surfactant and/or of synthetic emulsifying polymer means compositions containing less than 1%, preferably less than 0.5% or even less than 0.2% by weight, or 0% by weight, of surfactant and/or of synthetic emulsifying polymer.

The composition of the invention may also comprise at least one cosmetic adjuvant chosen from cosmetic or dermatological active agents, preserving agents, antioxidants, fragrances, fillers, UV-screening agents, pigments, odour absorbers and dyestuffs.

In particular, it will comprise at least one active agent chosen from moisturizers; free-radical scavengers; keratolytic and desquamating agents; vitamins; anti-elastase and anti-collagenase agents; trace elements; algal or plankton extracts; enzymes and coenzymes; flavonoids and isoflavonoids; ceramides; anti-glycation agents; NO-synthase inhibitors; agents for stimulating the synthesis of dermal or epidermal macromolecules and/or for preventing their degradation; agents for stimulating fibroblast or keratinocyte proliferation and/or keratinocyte differentiation; tensioning agents; anti-pollution agents and/or free-radical scavengers; muscle relaxants or dermo-decontracting agents; and mixtures thereof.

According to one embodiment of the invention, the composition also comprises at least one UV-screening agent, preferably at least one lipophilic or liposoluble UV-screening agent.

Among the lipophilic UV-screening agents that may be used according to the invention, mention may be made of those chosen from anthranilates; cinnamic derivatives; dibenzoylmethane derivatives; salicylic derivatives; camphor derivatives; triazine derivatives such as those described in patent applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives, especially those mentioned in U.S. Pat. No. 5,624,663; benzimidazole derivatives; imidazolines; p-aminobenzoic acid (PABA) derivatives; benzoxazole derivatives such as those described in patent applications EP 0 832 642, EP 1 027 883, EP 1 300 137 and DE 101 62 844; screening polymers such as those described especially in patent application WO 93/04665; α-alkylstyrene-based dimers such as those described in patent application DE 198 55 649, 4,4-diarylbutadienes such as those described in patent applications DE 197 55 649, EP 916 335, EP 1 133 980, EP 1 133 981 and EP-A-1 008 586, and mixtures thereof.

As examples of lipophilic organic screening agents, mention may be made of those denoted above under their INCI name:
para-Aminobenzoic Acid Derivatives:
Ethyl PABA,
Ethyl dihydroxypropyl PABA, Ethylhexyl dimethyl PABA sold in particular under the name Escalol 507 by ISP, Salicylic Derivatives:

Homosalate sold under the name Eusolex HMS by Rona/EM Industries,

Ethylhexyl salicylate sold under the name Neo Heliopan OS by Haarmann and Reimer, TEA salicylate sold under the name Neo Heliopan TS by Haarmann and Reimer, Dibenzoylmethane Derivatives:

Butyl methoxydibenzoylmethane sold in particular under the trade name Parsol 1789 by Hoffmann LaRoche, Isopropyldibenzoylmethane, Cinnamic Derivatives:

Ethylhexyl methoxycinnamate sold in particular under the trade name Parsol MCX by Hoffmann LaRoche, Isopropyl methoxycinnamate, Isoamyl methoxycinnamate sold under the trade name Neo Heliopan E 1000 by Haarmann and Reimer, Cinoxate, Diisopropyl methylcinnamate, β,β-Diphenylacrylate Derivatives:

Octocrylene sold in particular under the trade name Uvinul N539 by BASF,

Etocrylene sold in particular under the trade name Uvinul N35 by BASF,

Benzophenone Derivatives:

Benzophenone-1 sold under the trade name Uvinul 400 by BASF,

Benzophenone-2 sold under the trade name Uvinul D50 by BASF,

Benzophenone-3 or Oxybenzone sold under the trade name Uvinul M40 by BASF,

Benzophenone-6 sold under the trade name Helisorb 11 by Norquay,

Benzophenone-8 sold under the trade name Spectra-Sorb UV-24 by American Cyanamid, Benzophenone-9 sold under the trade name Uvinul DS-49 by BASF, n-Hexyl 2-(4-diethylamino-2-hydroxybenzoyl)benzoate, Benzylidenecamphor Derivatives:

3-Benzylidenecamphor manufactured under the name Mexoryl SD by Chimex,

4-Methylbenzylidenecamphor sold under the name Eusolex 6300 by Merck,

Triazine Derivatives:

Bis-ethylhexyloxyphenyl methoxyphenyl triazine sold under the trade name Tinosorb S by Ciba Geigy, Ethylhexyltriazone sold in particular under the trade name Uvinul T150 by BASF, Diethylhexylbutamidotriazone sold under the trade name Uvasorb HEB by Sigma 3V, 2,4,6-Tris(dineopentyl 4'-aminobenzalmalonate)-s-triazine, 2,4,6-Tris(diisobutyl 4'-aminobenzalmalonate)-s-triazine, Benzotriazole Derivatives:

Drometrizole trisiloxane sold under the name Silatrizole by Rhodia Chimie,

Anthranilic Derivatives:

Menthyl anthranilate sold under the trade name Neo Heliopan MA by Haarmann and Reimer, Imidazoline Derivatives:

Ethylhexyldimethoxybenzylidenedioxoimidazoline propionate,

Benzalmalonate Derivatives:

Dineopentyl 4'-methoxybenzalmalonate, 4,4-Diarylbutadiene Derivatives:

1,1-Dicarboxy(2',2'-dimethylpropyl)-4,4-diphenyl-butadiene,

Benzoxazole Derivatives:

2,4-Bis[5-1(dimethylpropyl)benzoxazol-2-yl(4-phenyl)imino]-6-(2-ethylhexyl)imino-1,3,5-triazine sold under the name Uvasorb K2A by Sigma 3V, and mixtures thereof.

The lipophilic organic screening agents that are more particularly preferred are chosen from the following compounds:

Homosalate,

Ethylhexyl salicylate,

Ethylhexyl methoxycinnamate,

Octocrylene,

Butyl methoxydibenzoylmethane,

Benzophenone-3, n-Hexyl 2-(4-diethylamino-2-hydroxybenzoyl)benzoate,

4-Methylbenzylidenecamphor, 2,4,6-Tris(dineopentyl 4'-aminobenzalmalonate)-s-triazine, 2,4,6-Tris(diisobutyl 4'-aminobenzalmalonate)-s-triazine, Bis-ethylhexyloxyphenyl methoxyphenyl triazine, Ethylhexyl triazone, Diethylhexyl butamido triazone, Drometrizole trisiloxane, Dineopentyl 4'-methoxybenzalmalonate, 1,1-Dicarboxy(2',2'-dimethylpropyl)-4,4-diphenyl-butadiene, 2,4-Bis[5-1(dimethylpropyl)benzoxazol-2-yl(4-phenyl)imino]-6-(2-ethylhexyl)imino-1,3,5-triazine and mixtures thereof.

The said screening agents are even more preferentially chosen from:

Homosalate,

Ethylhexyl salicylate,

Ethylhexyl methoxycinnamate,

Octocrylene,

Butyl methoxydibenzoylmethane,

Ethylhexyl triazone,

Bis-ethylhexyloxyphenyl methoxyphenyl triazine,

Diethylhexyl butamido triazone,

Drometrizole trisiloxane.

The lipophilic screening agents in accordance with the invention are preferably present in the compositions according to the invention in a content ranging from 0.1% to 30% by weight and preferably from 0.5% to 15% by weight relative to the total weight of the composition.

Preferably, the composition according to the invention comprises at least 2% by weight, preferably at least 5% by weight and even more preferentially at least 10% by weight of UV-screening agent relative to the total weight of the composition.

The composition according to the invention advantageously contains at least one cosmetic or dermatological active agent.

Ingredients and/or active agents of natural origin will advantageously be used.

As fillers that may be used in the composition of the invention, examples that may be mentioned include powders of natural organic materials such as corn, wheat or rice starch; or alternatively materials of natural mineral origin, for instance silica, talc, clays, for instance kaolin, montmorillonite, saponites, laponites and illites.

The amount of fillers is preferably less than or equal to 20% of the total weight of the composition, better still less than or equal to 10% of the total weight of the composition, preferably less than or equal to 8%, or even less than or equal to 5% of the total weight of the composition. When they are present, these fillers may be present in amounts ranging, for example, from 0.05% to 8% by weight and preferably from 0.1% to 5% by weight relative to the total weight of the composition.

When the composition is used in the field of makeup, it may contain any filler, dye or pigment usually used in the field of makeup.

As cosmetic or dermatological active agents that may be used in the composition according to the invention, mention may be made especially of moisturizers; free-radical scavengers; keratolytic and desquamating agents; vitamins; anti-elastase and anti-collagenase agents; trace elements; algal or plankton extracts; enzymes and coenzymes; flavonoids and isoflavonoids; ceramides; anti-glycation agents; NO-synthase inhibitors; agents for stimulating the synthesis of dermal or epidermal macromolecules and/or for preventing their degradation; agents for stimulating fibroblast or keratinocyte proliferation and/or keratinocyte differentiation; tensioning agents; anti-pollution agents and/or free-radical scavengers; muscle relaxants or dermo-decontracting agents; and mixtures thereof.

Examples of active agents that may be mentioned include (N-2-hydroxyethylpiperazine-N-2-ethane)sulfonic acid (HEPES); hyaluronic acid; lanolin; urea and mixtures containing urea, such as NMF (Natural Moisturizing Factor), and urea derivatives such as N-(2-hydroxy-ethyl)urea (Hydrovance from the company National Starch); 2-oxothiazolidine-4-carboxylic acid (procysteine); α-hydroxy acids, especially fruit-based acids, for instance glycolic acid, lactic acid, malic acid, citric acid, tartaric acid or mandelic acid, and derivatives and mixtures thereof; β-hydroxy acids, for instance salicylic acid and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate and magnesium or sodium ascorbyl phosphate; its esters, for instance ascorbyl acetate, ascorbyl palmitate and ascorbyl propionate, or its sugars, for instance glycosyl ascorbic acid, and mixtures thereof; β-keto acids; retinoids, for instance retinol (vitamin A) and its esters, retinal, retinoic acid and its derivatives, and also the retinoids described in documents FR-A-2 570 377, EP-A-199 636, EP-A-325 540, EP-A-402 072, EP-A-325 540 and EP-A-402 072; carotenoids such as lycopene; ceramides; sapogenins and plant extracts containing them, in particular extracts of wild yam; resveratrol; pseudodipeptides such as {2-[acetyl(3-trifluoromethylphenyl)amino]-3-methylbutyryl-amino}acetic acid; vitamins, for instance, besides vitamins A and C indicated above, vitamin E (tocopherol), vitamin B3 (or vitamin PP or niacinamide), vitamin B5 (panthenol in its various forms: D-panthenol, DL-panthenol), vitamin D and vitamin F (mixture of essential fatty acids), and derivatives, precursors and analogues of these vitamins; soybean extracts, in particular soybean protein hydrolysates or isoflavone-rich soybean extracts; trace elements, for instance copper, zinc, selenium, iron, magnesium or manganese; algal extracts, for instance the product sold under the name Stimoderm by the company CLR; plankton extracts such as the plankton in aqueous dispersion (CTFA name: Vitreoscilla ferment) sold under the name Mexoryl SAH by the company Chimex; enzymes; coenzymes such as ubiquinone or coenzyme Q10 which belongs to the family of benzoquinones containing an alkylene chain, coenzyme R, which is biotin (or vitamin H); yeast extracts, for instance the extract of S. cerevisiae sold under the name Cytovitin LS 9388 by Laboratoires Sérobiologiques; adenosine; plant extracts, for instance extracts of liquorice; calmatives, for instance bisabolol and calmative plant extracts, for instance extracts of rose (*Rosa gallica*) and extracts of mint (*Mentha piperita*); and any active agent that is suitable for the final aim of the composition, and mixtures thereof.

The ingredients and/or active agents will be present in the composition in contents ranging from 0.01% to 20% by weight, preferably 0.05% to 10% and even more preferentially from 0.1% to 1% by weight relative to the total weight of the composition.

These ingredients and/or active agents and the concentrations thereof must be such that they do not modify the property desired for the composition of the invention.

The composition according to the invention finds its application in a large number of treatments, especially cosmetic treatments for the skin, including the scalp, the hair, the nails and/or mucous membranes, in particular for caring for, cleansing and/or making up and/or sun-protecting the skin and/or mucous membranes.

Thus, a subject of the present invention is the cosmetic use of the composition as defined above, for treating, protecting, caring for, removing makeup from and/or cleansing the skin, the lips and/or the hair, and/or for making up the skin and/or the lips.

A subject of the present invention is also a non-therapeutic process for caring for, making up or removing makeup from the skin, including the scalp, the hair and/or the lips, comprising the application to the skin, the hair and/or the lips of a composition as defined above.

In particular, the composition according to the invention is used for caring for and/or treating dry and/or sensitive skin.

Cosmetic Assembly

According to another aspect, the invention also relates to a cosmetic assembly comprising:
  i) a container delimiting at least one compartment, the said container being closed by means of a closing member; and
  ii) a composition as described above, placed inside the said compartment.

The container may be in any adequate form. It may especially be in the form of a bottle, a tube, a jar, a case, a box, a sachet or a carton.

The closing member may be in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The container may be combined with an applicator. The applicator may be in the form of a fine brush, as described, for example, in patent FR 2 722 380. The applicator may be in the form of a block of foam or of elastomer, a felt or a spatula. The applicator may be free (tuft or sponge) or securely fastened to a rod borne by the closing member, as described, for example, in U.S. Pat. No. 5,492,426. The applicator may be securely fastened to the container, as described, for example, in patent FR 2 761 959.

The product may be contained directly in the container, or indirectly. By way of example, the product may be arranged on an impregnated support, especially in the form of a wipe or a pad, and arranged (individually or in plurality) in a box or in a sachet. Such a support incorporating the product is described, for example, in patent application WO 01/03538.

The closing member may be coupled to the container by screwing. Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of thermoplastic materials that may be mentioned include polypropylene or polyethylene.

Alternatively, the container is made of non-thermoplastic material, especially glass or metal (or alloy).

The container may have rigid walls or deformable walls, especially in the form of a tube or a tubular bottle.

The container may comprise means for initiating or facilitating the distribution of the composition. By way of example, the container may have deformable walls so as to allow the composition to exit in response to a positive pressure inside the container, this positive pressure being caused by elastic (or non-elastic) squeezing of the walls of the container.

The container may consist of a carton with a base delimiting at least one housing containing the composition, and a lid, especially articulated on the base, and capable of at least partially covering the said base. Such a carton is described, for example, in patent application WO 03/018423 or in patent FR 2 791 042.

The container may be equipped with a drainer arranged in the region of the aperture of the container. Such a drainer makes it possible to wipe the applicator and possibly the rod to which it may be securely fastened. Such a drainer is described, for example, in patent FR 2 792 618.

The examples hereinbelow of compositions according to the invention are given as non-limiting illustrations. The compounds are indicated as their chemical name or as their INCI name. The amounts therein are given as weight percentages, unless otherwise mentioned.

Examples: Examples of Formulations

Nutritive Moisturizing Care Fluid

|  |  | % |
|---|---|---|
| Phase A | Preserving agent | qs |
|  | Glycerol | 5 |
|  | Water | qs 100 |
|  | Cetyl hydroxyethylcellulose (Polysurf 67 from the company Aqualon) | 1 |
|  | Lauryl inulin carbamate (Inutec SP1 from the company Orafti)* | 0.1 |
| Phase B | Apricot kernel oil | 5 |
|  | Sweet almond oil | 5 |

*= Inutec SP1 from the company Orafti containing 96.5% by weight of lauryl inulin carbamate active material (i.e. in the composition 0.1% by weight of starting material and 0.0965% by weight of active material)

Procedure

Preparation of phase A by dispersing the starting materials in water with stirring at 70° C. Homogenization until a smooth gel is obtained.

Emulsification at about 52° C. by dispersing the oily phase in the aqueous phase with stirring.

A milk is obtained, which melts on the skin giving, when applied, a soothing moisturizing effect.

Nutritive Fluid Cream

|  |  | % |
|---|---|---|
| Phase A | Preserving agent | qs |
|  | Glycerol | 5 |
|  | Water | qs 100 |
|  | Cetyl hydroxyethylcellulose (Polysurf 67 from the company Aqualon) | 1.2 |
|  | Inutec SP1 from the company Orafti* | 0.2 |
| Phase B | Apricot kernel oil | 5 |
|  | Dicaprylyl ether of plant origin (Cetiol OE from the company Cognis) | 7.5 |
|  | Plant perhydrosqualene | 7.5 |

*= Inutec SP1 from the company Orafti containing 96.5% by weight of lauryl inulin carbamate active material Procedure Preparation of phase A by dispersing the starting materials in water with stirring at 70° C. Homogenization until a smooth gel is obtained.

Emulsification at about 52° C. by dispersing the oily phase in the aqueous phase with stirring.

A soft cream is obtained, which melts on the skin giving, when applied, a soothing and nutritive effect.

Mild Makeup-Removing Milks

|  |  | Ex. A % | Ex. B % |
|---|---|---|---|
| Aqueous Phase A | Preserving agent | qs | qs |
|  | Glycerol | 5 | 5 |
|  | Water | qs 100 | qs 100 |
|  | Lauryl inulin carbamate (Inutec SP1 from the company Orafti)* | 0.8 | 0.8 |
|  | Tapioca starch (National Starch) | 1 |  |
|  | Mixture of gums of plant origin (mannan gum) and biotechnological origin (xanthan gum) (Glucovis from the company Chesham Chemicals Ltd) |  | 0.5 |
| Oily Phase B | Dicaprylyl ether | 15 | 15 |
|  | Isopropyl myristate | 15 | 15 |
| C | Alcohol | 5 | 5 |

*= Inutec SP1 from the company Orafti containing 96.5% by weight of lauryl inulin carbamate active material Procedure Preparation of phase A by dispersing the starting materials in water with stirring at 70° C. Homogenization until a smooth gel is obtained.

Emulsification by dispersing the oily phase in the aqueous phase with stirring.

After cooling, addition of the alcohol. Makeup-removing milks are obtained, which give, when applied, a soft effect on the skin.

The invention claimed is:

1. A composition, comprising:
   a) at least 0.01% by weight, relative to the total weight of the composition, of at least one inulin modified with hydrophobic chains, and
   b) at least 0.05% by weight, relative to the total weight of the composition, of at least one thickening polysaccharide of plant origin, wherein the at least one thickening polysaccharide of plant origin is a $(C_1-C_3)$ hydroxyalkyl cellulose modified with hydrophobic chains comprising from 8 to 30 carbon atoms, the hydrophobic chain modifying the at least one inulin comprises an alkyl carbamate group of formula (I):

$$R-NH-CO- \qquad (I)$$

wherein R is an alkyl group having 1 to 22 carbon atoms, the composition is an oil in water emulsion having an inner fatty phase and an outer aqueous phase, the composition does not comprise a silicone, and the composition does not comprise an emulsifying polymer of petrochemical or synthetic origin and does not comprise a thickening polymer of petrochemical or synthetic origin.

2. The composition according to claim 1, wherein the inner fatty phase is at least 2% by weight relative to the total weight of the composition.

3. The composition according to claim 1, wherein the inulin modified with hydrophobic chains is from 0.01% to 20% by weight relative to the total weight of the composition.

4. The composition according to claim 1, wherein an inulin modified with hydrophobic chains/inner fatty phase weight ratio is from 1:0.1 to 0.1:60.

5. The composition according to claim 1, wherein the hydrophobic chains are lauryl carbamate groups.

6. The composition according to claim 1, comprising at least two thickening polysaccharides of plant origin.

7. The composition according to claim 1, wherein the polysaccharide is from 0.05% to 10% by weight relative to the total weight of the composition.

8. The composition according to claim 1, wherein the composition is free of surfactant.

9. A non-therapeutic process for caring for, making up or removing makeup from the skin, the scalp, the hair and/or the lips, comprising applying to the skin, the hair and/or the lips a composition according to claim 1.

* * * * *